(12) United States Patent
Takemoto et al.

(10) Patent No.: US 10,295,513 B2
(45) Date of Patent: May 21, 2019

(54) FERRULE CONTAINER, AND FERRULE CONTAINER CONTAINING FERRULE

(71) Applicant: Shimadzu Corporation, Kyoto (JP)

(72) Inventors: Hajime Takemoto, Kyoto (JP); Hirokazu Taniuchi, Kyoto (JP); Yoshihiko Ide, Kyoto (JP); Masayuki Okada, Kyoto (JP); Yasunori Terai, Kyoto (JP)

(73) Assignee: Shimadzu Corporation, Nishinokyo-Kuwabaracho, Nakagyo-ku, Kyoto-shi, Kyoto (JP)

(*) Notice: Subject to any disclaimer, the term of this patent is extended or adjusted under 35 U.S.C. 154(b) by 241 days.

(21) Appl. No.: 15/310,571

(22) PCT Filed: May 15, 2014

(86) PCT No.: PCT/JP2014/062980
§ 371 (c)(1),
(2) Date: Nov. 11, 2016

(87) PCT Pub. No.: WO2015/173933
PCT Pub. Date: Nov. 19, 2015

(65) Prior Publication Data
US 2017/0082584 A1    Mar. 23, 2017

(51) Int. Cl.
*B65D 85/30* (2006.01)
*G01N 30/60* (2006.01)
(Continued)

(52) U.S. Cl.
CPC ........... *G01N 30/60* (2013.01); *B01D 53/025* (2013.01); *B65D 65/02* (2013.01); *B65D 75/36* (2013.01);
(Continued)

(58) Field of Classification Search
CPC ........ B65D 65/02; B65D 75/36; G01N 30/60; G01N 30/6034; G01N 30/6039; G01N 2030/025; B01D 53/025
(Continued)

(56) References Cited

U.S. PATENT DOCUMENTS 2,878,932 A * 3/1959 Martire, Jr. ............ A47G 23/06
                                                                206/564
4,300,674 A * 11/1981 Davet ...................... A47F 7/024
                                                                206/1.5
(Continued)

OTHER PUBLICATIONS

Office Action from the Chinese Patent Office dated Aug. 2, 2017 for corresponding patent application 201480078875.1.

*Primary Examiner* — Luan K Bui
(74) *Attorney, Agent, or Firm* — Muir Patent Law, PLLC

(57) ABSTRACT

A ferrule container 1 is provided with a ferrule accommodating part 11 and a first column guide part 12. A ferrule is accommodated in the ferrule accommodating part 11. The first column guide part 12 guides a column so as to insert the column into the ferrule accommodated in the ferrule accommodating part 11. Guiding of the column by the first column guide part 12 enables the column to be smoothly and reliably inserted into the ferrule accommodated in the ferrule accommodating part 11. Consequently, unlike a case in which an operator inserts a column while pinching a ferrule with hand, the work of inserting a column into a ferrule can easily be performed.

7 Claims, 9 Drawing Sheets

(51) Int. Cl.
  *B01D 53/02*   (2006.01)
  *B65D 65/02*   (2006.01)
  *B65D 75/36*   (2006.01)
  *G01N 30/02*   (2006.01)

(52) U.S. Cl.
  CPC ..... *G01N 30/6039* (2013.01); *G01N 30/6034* (2013.01); *G01N 2030/025* (2013.01)

(58) Field of Classification Search
  USPC ................ 206/701, 722–725, 338, 493, 564
  See application file for complete search history.

(56) References Cited

U.S. PATENT DOCUMENTS

| | | | | |
|---|---|---|---|---|
| 5,775,484 | A * | 7/1998 | Ovadia | ............... A47F 7/02 |
| | | | | 206/560 |
| 6,554,137 | B1 * | 4/2003 | Fratti | ............... H01L 23/60 |
| | | | | 206/701 |
| 6,932,212 | B2 * | 8/2005 | Ovadia | ............... A47F 7/02 |
| | | | | 206/482 |
| 7,537,109 | B1 * | 5/2009 | Shevick | ........... B65D 25/106 |
| | | | | 206/482 |
| 8,128,131 | B2 | 3/2012 | Barnett et al. | |
| 2005/0211098 | A1 | 9/2005 | Shimomura | |
| 2008/0202980 | A1 * | 8/2008 | Su | ...................... B65D 85/48 |
| | | | | 206/701 |
| 2011/0192751 | A1 * | 8/2011 | Doster | ............... B65D 5/503 |
| | | | | 206/459.5 |

\* cited by examiner

FERRULE CONTAINER, AND FERRULE CONTAINER CONTAINING FERRULE

TECHNICAL FIELD

The present invention relates to a ferrule container for accommodating a ferrule, and also to a ferrule container containing a ferrule using the same.

BACKGROUND ART

In a gas chromatograph, a carrier gas is introduced into a column from a sample introduction part together with a sample, and each sample component is separated during the passing of the carrier gas through the column. Each sample component separated in the column is detected by a detector connected to the column. The connection of the column to the sample introduction part or the detector can be performed via a column attachment device.

The column attachment device is provided with, for example, a ferrule, a ferrule receiving part, and a ferrule pressing part. The ferrule is attached to the column by being swaged in a state in which the column is inserted. And, by fixing the ferrule attached to the column by pinching between the ferrule receiving part and the ferrule pressing part, the column can be attached to the column attachment device (see, for example, the following Patent Document 1).

A ferrule is a very small piece, which is carried in a state in which it is accommodated in a ferrule container, and used by taking out of the ferrule container as the need arises. FIG. 7 is a perspective view showing a configuration example of a conventional ferrule container 100. Further, FIG. 8 is a cross-sectional view partially showing the C-C cross-section of the ferrule container 100 shown in FIG. 7.

As shown in FIGS. 7 and 8, a conventional ferrule container 100 has a shape similar to a shape of a tablet container. Namely, the ferrule container 100 is configured by, for example, a transparent plastic container in which a plurality of ferrule accommodating parts 102 for accommodating ferrules 101 are formed as concave portions.

In each ferrule accommodating part 102, a circular interior space 103 slightly larger than the ferrule 101 is formed. The ferrule 101 is accommodated in the ferrule accommodating part 102 in a laid state so as not to protrude from the interior space 103. One sheet of cover film 104 is adhered to the ferrule container 100, so that each ferrule accommodating part 102 is covered by the cover film 104.

At the time of using the ferrule 101, the cover film 104 is broken at a portion corresponding to any ferrule accommodating part 102 to open the interior space 103 in the ferrule accommodating part 102. Thus, the ferrule 101 can be taken out of the interior space 103. Then, an operator performs an operation of inserting a column into the ferrule 101 taken out of the ferrule container 100 and then swaging the ferrule 101. Thus, the ferrule 101 can be attached to the column.

PRIOR ART DOCUMENT

Patent Document

Patent Document 1: U.S. Pat. No. 8,128,131

SUMMARY OF THE INVENTION

Problems to be Solved by the Invention

In the conventional configuration as mentioned above, however, the operation of inserting the column into the ferrule 101 taken out of the ferrule container 100 by an operator was troublesome. Especially, the ferrule 101 is a very small part, for example, having an outer diameter of about 3 mm, and therefore there is a problem that the operation of inserting the column into the insertion hole (e.g., the inner diameter is 0.8 mm or less) in the ferrule 101 is very difficult.

Further, an operator performs the aforementioned operation of inserting the column while pinching the ferrule 101 by hand, which is likely to cause adherence of foreign objects to the ferrule 101. For this reason, since an analysis is performed using the ferrule 101 to which foreign objects are adhered, there is a problem that analysis results are likely to be adversely influenced.

The present invention was made in view of the aforementioned circumstances, and aims to provide a ferrule container and a ferrule container containing a ferrule capable of easily performing an operation of inserting a column into a ferrule. Further, the present invention also aims to provide a ferrule container in which foreign objects are less likely to adhere to the ferrule and a ferrule container containing a ferrule.

Means for Solving the Problems

A ferrule container according to the present invention is a ferrule container for accommodating a ferrule, and is provided with a ferrule accommodating part and a first column guide part. In the ferrule accommodating part, a ferrule is accommodated. The first column guide part guides a column so as to insert the column into the ferrule accommodated in the ferrule accommodating part.

With this configuration, guiding of the column by the first column guide part enables a smooth and reliable insertion of the column into the ferrule accommodated in the ferrule accommodating part. Consequently, unlike a case in which an operator inserts a column while pinching a ferrule with hand, the insertion work of a column into a ferrule can be easily performed.

Further, the insertion work of a column into a ferrule can be performed while keeping a state in which the ferrule is accommodated in the ferrule accommodating part. That is, since there is no need for an operator to bring his/her hand into contact with the ferrule during the insertion work of the column into the ferrule, foreign objects are less likely to adhere to the ferrule unlike a case in which an operator inserts a column while pinching the ferrule with hand.

The ferrule accommodating part may be configured to accommodate a ferrule in an inclined posture. In this case, the first column guide part may include a first inclined surface that gradually lowers as it advances toward the ferrule accommodating part.

According to this configuration, guiding of the column along the first inclined surface enables an oblique downward insertion of the column into the ferrule accommodated in the ferrule accommodating part in an inclined posture. With this, since the column can be easily inserted into the ferrule from above the ferrule container, the work for inserting the column into the ferrule can be easily performed.

The ferrule container may be further provided with a second column guide part for guiding the tip end part of the column inserted into the ferrule.

With this configuration, since the tip end part of the column inserted into the ferrule is guided by the second column guide part, the tip end part becomes a state in which the tip end part is sufficiently protruded from the ferrule. Therefore, at the time of taking out the ferrule from the ferrule container together with the column after inserting the column into the ferrule, it is possible to prevent the column from being dropped from the ferrule. As a result, the insertion work of the column into the ferrule can be more easily performed.

The second column guide part may include a second inclined surface that gradually becomes higher as it gets away from the ferrule accommodating part.

With this configuration, the tip end part of the column inserted into the ferrule becomes a curved state during the tip end part is guided along the second inclined surface. When the column is further inserted into the ferrule, the ferrule can be lifted up from the ferrule accommodating part by the restoring force of the column. With this, after inserting the column into the ferrule, the ferrule can be smoothly taken out from the ferrule container together with the column. Therefore, the work for inserting the column into the ferrule can be more easily performed.

This ferrule container containing a ferrule is provided with the ferrule container, and a ferrule accommodated in the ferrule accommodating part.

According to this configuration, it is possible to insert the column into the ferrule in a state in which the ferrule is accommodated in the ferrule accommodating part. With this, before inserting the column into the ferrule, it is not at all necessary for an operator to bring the hand into contact with the ferrule. Consequently, unlike a case in which an operator inserts a column while pinching a ferrule with hand, the insertion work of a column into a ferrule can be more easily performed, and foreign objects are much less likely to adhere to the ferrule.

The ferrule container may be provided with a plurality of ferrule accommodating parts. In this case, the ferrule container containing ferrules may be further provided with a plurality of cover films that individually cover each ferrule accommodating part and are each capable of being peeled from the ferrule container.

According to this configuration, by selecting either one of the plurality of ferrule accommodating parts and peeling off the cover film covering the ferrule accommodating part, a column can be inserted into the ferrule in the ferrule accommodating part. As described above, since only the cover film corresponding to the ferrule to be used can be peeled off, the remaining ferrules can be kept in a state in which they are covered by the cover films until the time of use, which can prevent adhering of foreign objects to the ferrules.

A conically-shaped dent may be formed at an end face of the ferrule on the first column guide part side so as to expand larger than an outer diameter of a column to be inserted so that the column is inserted into the ferrule via the dent. In this case, the column may be inserted into the ferrule via the dent.

According to such a configuration, the column guided by the first column guide part is smoothly inserted into the ferrule via the conically-shaped dent formed in the ferrule so as to expand larger than the outer diameter of the column. Therefore, the work for inserting the column into the ferrule can be performed more easily.

Effects of the Invention

According to the present invention, unlike a case in which an operator inserts a column while pinching a ferrule with hand, the insertion work of a column into a ferrule can be more easily performed, and foreign objects are much less likely to adhere to the ferrule.

EMBODIMENTS FOR CARRYING OUT THE INVENTION

Figure 1:
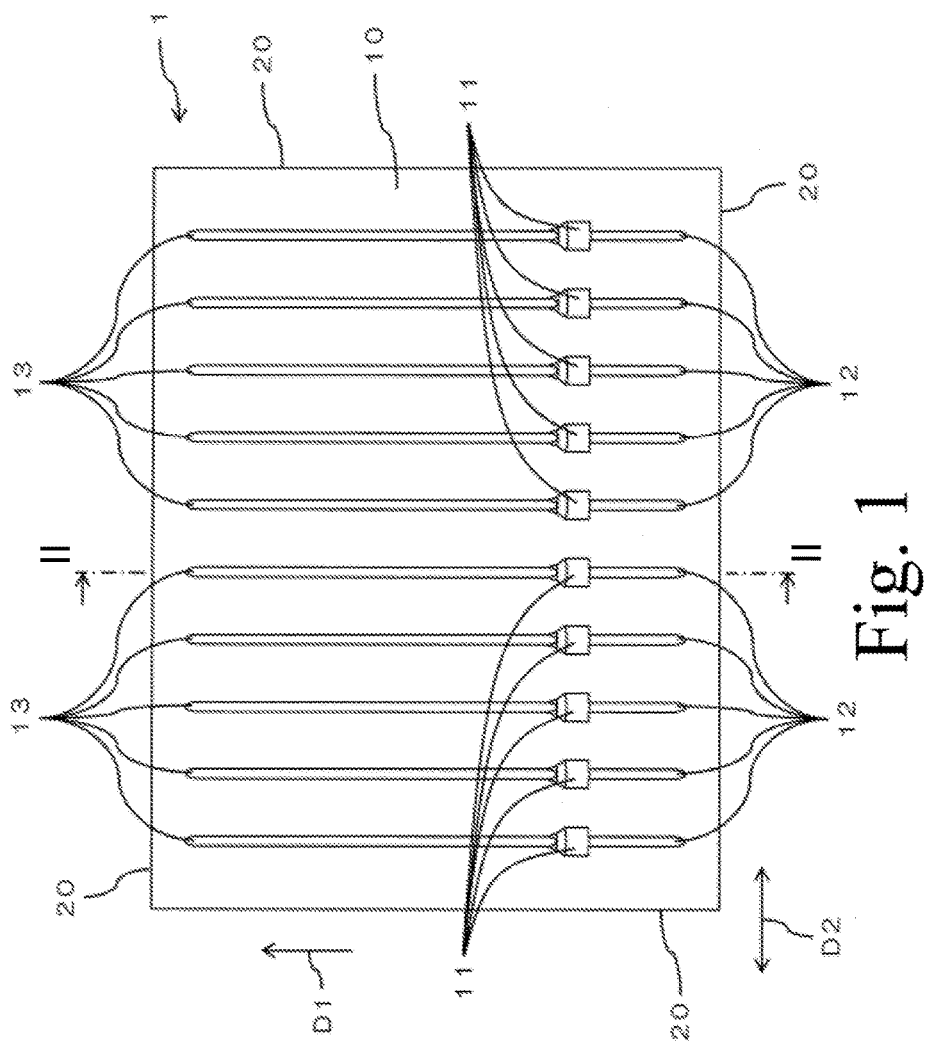
FIG. 1 is a plan view showing a configuration example of a ferrule container according to one embodiment of the present invention.
Figure 2:
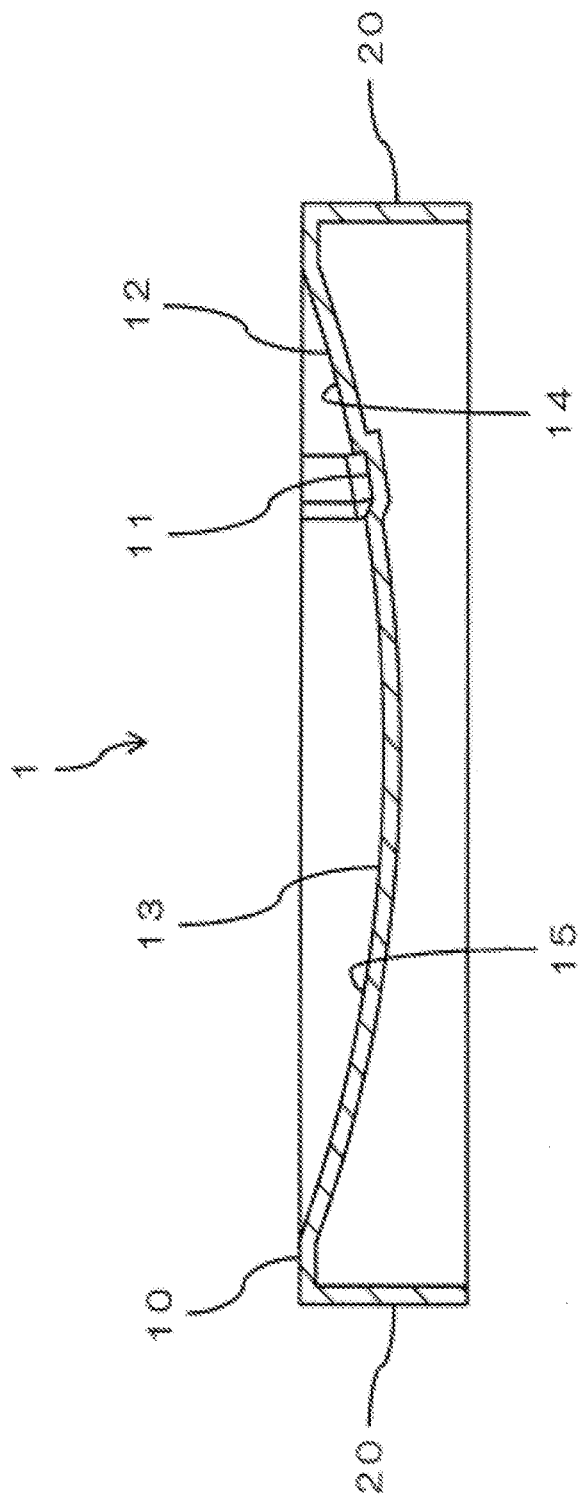
FIG. 2 is an II-II cross-sectional view of the ferrule container shown in FIG. 1.

FIG. 1 is a plan view showing a configuration example of a ferrule container 1 according to one embodiment of the present invention. Further, FIG. 2 is an A-A cross-sectional view of the ferrule container 1 shown in FIG. 1. This ferrule container 1 is a container for accommodating ferrules (not illustrated), and is configured by, for example, integrally forming a rectangular-shaped top wall 10 and four side walls 20 extending downward from four sides of the top wall 10 respectively.

In the top wall 10, for example, a plurality of accommodating parts 11 are formed. Each ferrule accommodating part 11 is configured by a concave portion having a shape slightly larger than a ferrule and accommodates the ferrule in the concave portion. As shown in FIG. 1, the ferrule accommodating parts 11 are arranged in a row at predetermined intervals in a width direction D2 perpendicular to the insertion direction D1 of a column to the ferrule. However, it is not limited to the configuration in which a plurality of ferrule accommodating parts 11 are provided in a ferrule container 1, and it may be configured such that, for example, only one ferrule accommodating part is provided in a ferrule container 1.

On the top wall 10, first column guide parts 12 and second column guide parts 13 are formed corresponding to respective ferrule accommodating parts 11. The first column guide part 12 and the second column guide part 13 are each formed by a concave portion having a width (length in the width direction D2) slightly larger than the outer diameter of a column, so that the column is guided in the concave portion.

The first column guide part 12 is, in the plan view shown in FIG. 1, provided at the upstream side (upstream side of the arrow in the insertion direction D1) in the insertion direction D1 of the column with respect to the ferrule accommodating part 11, and the end portion of the downstream side (downstream side of the arrow in the insertion direction D1) is connected to the ferrule accommodating part 11. A column is guided in the insertion direction D1 by the first column guide part 12 and inserted into the ferrule accommodated in the ferrule accommodating part 11. As shown in FIG. 2, the bottom surface of the first column guide part 12 is formed into a curved surface 14 in which the cross-section taken along the insertion direction D1 of a column is downwardly curved.

The second column guide part 13 is, in the plan view shown in FIG. 1, provided at the downstream side (downstream side of the arrow in the insertion direction D1) in the insertion direction D1 of the column with respect to the ferrule accommodating part 11, and the end portion of the upstream side (upstream side of the arrow in the insertion direction D1) is connected to the ferrule accommodating part 11. The tip end part of the column after inserted into the ferrule accommodated in the ferrule accommodating part 11 is guided by the second column guide part 13. As shown in FIG. 2, the bottom surface of the second column guide part 13 is formed into a curved surface 15 in which the cross-section taken along the insertion direction D1 of a column is downwardly curved.

The height of the side wall 20 is higher than the depth of the ferrule accommodating part 11, the first column guide part 12, and the second column guide part 13 from the top wall 10. When the lower end faces of the side walls 20 are placed on a mounting surface, the ferrule accommodating part 11, the first column guide part 12, and the second column guide part 13 always take the same posture to the mounting surface.

In this embodiment, guiding of a column by the first column guide part 12 enables a smooth and reliable insertion of the column into the ferrule accommodated in the ferrule accommodating part 11. Consequently, unlike a case in which an operator inserts a column while pinching a ferrule with hand, the insertion work of a column into a ferrule can be easily performed.

Further, the insertion work of a column into a ferrule can be performed while keeping a state in which the ferrule is accommodated in the ferrule accommodating part 11. That is, since there is no need for an operator to bring his/her hand into contact with the ferrule during the insertion work of the column into the ferrule, foreign objects are less likely to adhere to the ferrule unlike a case in which an operator inserts a column while pinching the ferrule with hand.

Further, in this embodiment, since the tip end part of the column after inserted into the ferrule is guided by the second column guide part 13, the tip end part becomes a state in which the tip end part is sufficiently protruded from the ferrule. Therefore, at the time of taking out the ferrule from the ferrule container 1 together with the column after inserting the column into the ferrule, it is possible to prevent the column from being dropped from the ferrule. As a result, the insertion work of the column into the ferrule can be more easily performed.

Figure 3:
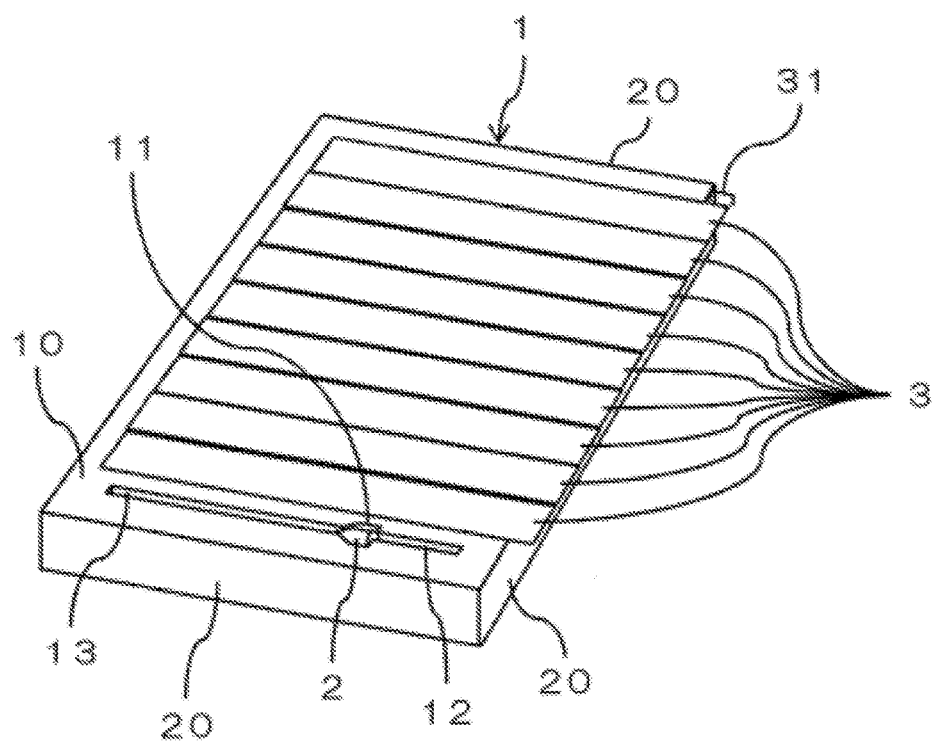
FIG. 3 is a perspective view showing a configuration example of a ferrule container containing ferrules in which ferrules are accommodated in the ferrule container shown in FIG. 1.

FIG. 3 is a perspective view showing a configuration example of a ferrule container containing ferrules in which ferrules are accommodated in the ferrule container 1 shown in FIG. 1. This ferrule container containing ferrules is configured such that ferrules 2 are accommodated in respective ferrule accommodating parts 11 of the ferrule container 1 and the ferrule accommodating parts 11 are individually covered by cover films 3. Each cover film 3 covers not only each ferrule accommodating part 11 but also the first column guide part 12 and the second column guide part 13 connected each ferrule accommodating part 11.

Each cover film 3 is a thin film formed by, for example, an aluminum foil, and peelably adhered to the upper surface of the top wall 10 of the ferrule container 1. At the time of using the ferrule 2, as shown in FIG. 3, the ferrule accommodating part 11 can be opened by peeling off the cover film 3 covering either ferrule accommodating part 11 from the ferrule container 1.

In this example, the majority of each cover film 3 is adhered to the top wall 10 of the ferrule container 1, and a part of each cover film 3 is protruded outward from the top wall 10 of the ferrule container 1. The portion of each cover film 3 protruded from the top wall 10 of the ferrule container 1 constitutes a grip portion 31 to be gripped by an operator. When an operator pulls the grip portion of each film 3 upward with the grip portion 31 gripped, each cover film 3 can be easily peeled off.

As described above, in this embodiment, by selecting either one of the plurality of ferrule accommodating parts 11 and peeling off the cover film 3 covering the ferrule accommodating part 11, a column can be inserted into the ferrule 2 in the ferrule accommodating part 11. As described above, since only the cover film 3 corresponding to the ferrule 2 to be used can be peeled off, the remaining ferrules 2 can be kept in a state in which the remaining ferrules are covered by cover films 3 until the time of use, so that it is possible to prevent adhering of foreign obstacles to the ferrule 2.

Figure 4:
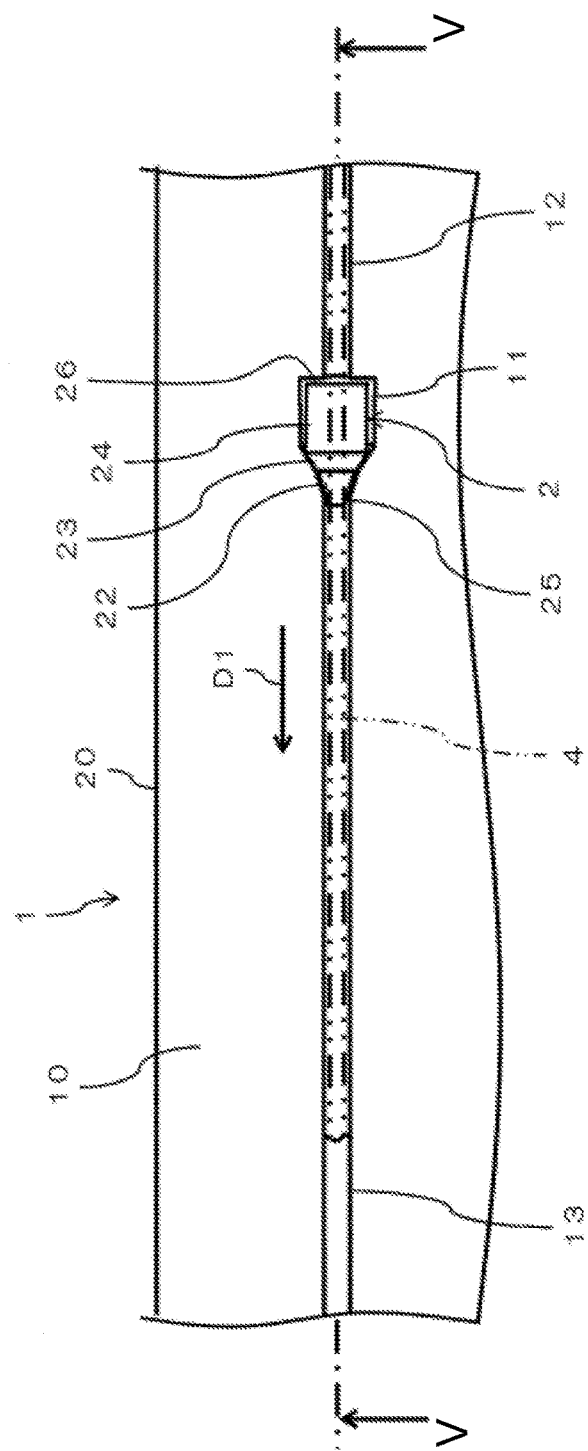
FIG. 4 is a partial plan view of the ferrule container containing ferrules shown in FIG. 3 and shows a state in which a cover film is peeled.
Figure 5:
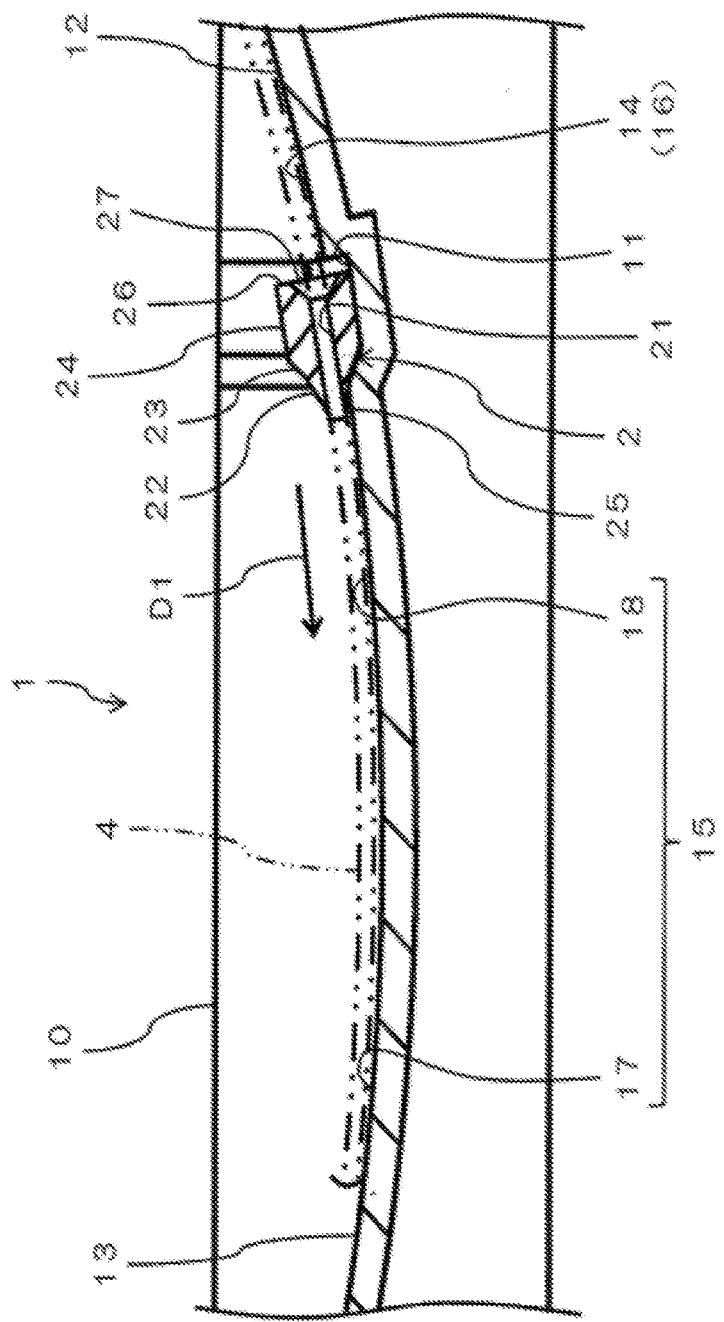
FIG. 5 is a V-V cross-sectional view of the ferrule container containing a ferrule shown in FIG. 4.

FIG. 4 is a partial plan view of the ferrule container containing a ferrule shown in FIG. 3 and shows a state in which a cover film 3 is peeled. Further, FIG. 5 is a B-B cross-sectional view of the ferrule container containing a ferrule shown in FIG. 4. The ferrule 2 is formed into, for example, a shape in which one end portion is tapered, and accommodated in the ferrule accommodating part 11 so that the one end portion faces the downstream side of the insertion direction D1 of the column 4. In this example, the ferrule 2 is accommodated in the ferrule accommodating part 11 in a posture in which the center axis line is inclined with respect to the horizontal direction.

The ferrule 2 is a cylindrical member in which an insertion hole 21 for inserting a column 4 along the center axis line is formed. The insertion hole 21 has an inner diameter (e.g., 0.8 mm or less) slightly smaller than the outer diameter of the column 4, and the column 4 is inserted into the insertion hole 21 from the upstream side of the insertion direction D1. On the outer peripheral surface of the ferrule 2, for example, a first conical surface 22, a second conical surface 23, and a cylindrical surface 24 are coaxially formed from the downstream side of the insertion direction D1 of the column 4 toward the upstream side thereof in this order.

The first conical surface 22 is formed into a tapered shape in which the outer diameter gradually decreases toward the downstream side of the insertion direction D1 of the column 4. At the tip end part of the first conical surface 22, a swaging part 25 to be swaged at the time of attaching the ferrule 2 to the column 4 is formed. Here, the wording "swage" denotes a work of attaching the ferrule 2 to the column 4 by plastically deforming the ferrule 2 by applying a pressure, and the swaging part 25 is swaged in a state in which the column 4 is inserted in the inner space of the ferrule 2, so that the ferrule 2 is attached to the column 4. The other end of the first conical surface 22 opposite to the swaging part 25 side is connected to the second conical surface 23.

The second conical surface 23 is formed into a tapered shape in which the outer diameter gradually decreases toward the downstream side of the insertion direction D1 of the column 4 in the same manner as the first conical surface 22. However, the inclination angle with respect to the central axis line is set to be larger than that of the first conical surface 22. Therefore, providing the second conical surface 23 having the inclination angle larger than the inclination angle of the first conical surface 22 while setting the inclination angle of the first conical surface 22 to an angle appropriate for swaging can make the length of the ferrule 2 along the central axis line shorter. The other end of the second conical surface 23 opposite to the first conical surface 22 side is connected to the cylindrical surface 24.

The cylindrical surface 24 has an uniform outer diameter (e.g., about 3 mm) along the central axis line of the ferrule 2. At the end face 26 of the cylindrical surface 24 side (first column guide part 12 side) of the ferrule 2, a conically-shaped dent 27 is formed so as to expand larger than the outer diameter of the column 4 to be inserted into the ferrule 2. The insertion hole 21 is expanded by the dent 27 toward the end face 26 side, so that the column 4 is smoothly inserted into the ferrule 2 from the end face 26 side via the dent 27. Therefore, the work for inserting the column 4 into the ferrule 2 can be performed more easily.

The ferrule accommodating part 11 is formed into a shape dented downwardly with respect to an extended line of the curved surface 14 of the first column guide part 12 extended toward the ferrule accommodating part 11 side and an extended line of the curved surface 15 of the second column guide part 13 extended toward the ferrule accommodating part 11. The insertion hole 21 of the ferrule 2 accommodated in the ferrule accommodating part 11 extends in a state of extending approximately along each of the extended lines of the first column guide part 12 and the second column guide part 13.

The shape of the ferrule accommodating part 11 corresponds to the shape of the outer peripheral surface of the ferrule 2. In this example, the ferrule accommodating part 11 is formed into a shape corresponding to the second conical surface 23 and the cylindrical surface 24 of the ferrule 2. However, the shape of the ferrule accommodating part 11 is not limited to the above, and any arbitrary shape may be employed as long as it is a shape capable of accommodating at least a part of the ferrule 2.

The shape of the ferrule 2 is not limited to the shape as shown in FIGS. 4 and 5, and any arbitrary shape may be employed. In other words, the shapes of the first conical surface 22, the second conical surface 23, the cylindrical surface 24, and the dent 27 are not limited to the shapes as shown in FIGS. 4 and 5. Further, it may be configured such that the second conical surface 23 or the dent 27 is omitted. Also, as to the shape of the insertion hole 21, it is not limited to a configuration of having an uniform inner diameter along the central axis line, but it may be configured such that the insertion hole 21 is formed by two or more holes different in inner diameter communicated with each other when the outer diameter of the column 4 is small, for example.

The curved surface 14 of the first column guide part 12 configures the first inclined surface 16 gradually lowered toward the ferrule accommodating part 11. On the other hand, the curved surface 15 of the second column guide part 13 includes a part (second inclined surface 17) gradually raised as it gets apart from the ferrule accommodating part 11 and a part (third inclined surface 18) that connects the part (second inclined surface 17) to the ferrule accommodating part 11 and is gradually lowered as it gets away from the ferrule accommodating part 11.

FIGS. 6A to 6D are schematic cross-sectional views for explaining an embodiment at the time of inserting a column 4 into a ferrule 2. When a column 4 is inserted into the ferrule 2 accommodated in the ferrule accommodating part 11 of the ferrule container 1, initially, the column 4 is guided along the first inclined surface 16 (see FIG. 6A).

With this, the column 4 can be inserted obliquely downward with respect to the ferrule 2 accommodated in the ferrule accommodating part 11 in an inclined posture. As a result, since the column 4 can be easily inserted into the ferrule 2 from above the ferrule container 1, the work for inserting the column 4 into the ferrule 2 can be easily performed.

Figure 6A:
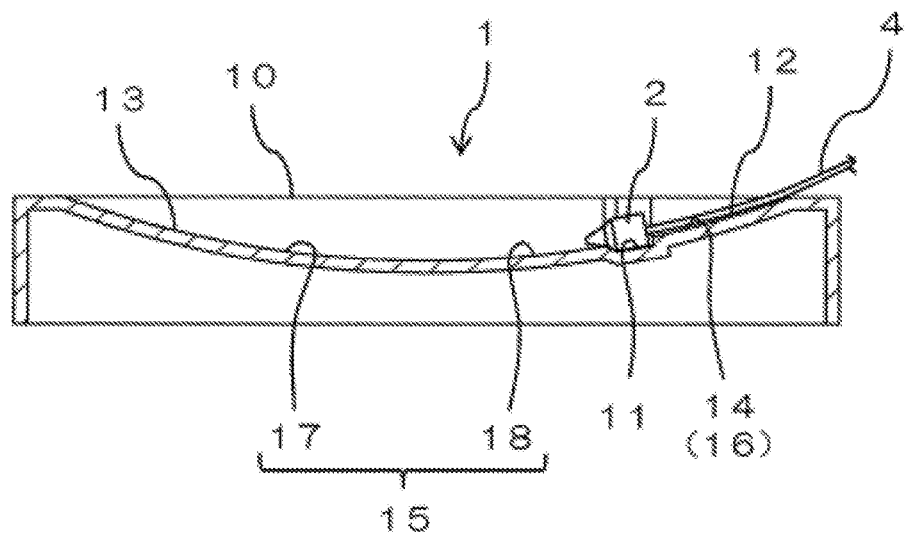
FIG. 6A is a schematic cross-sectional view for explaining an embodiment at the time of inserting a column into the ferrule.
Figure 6B:
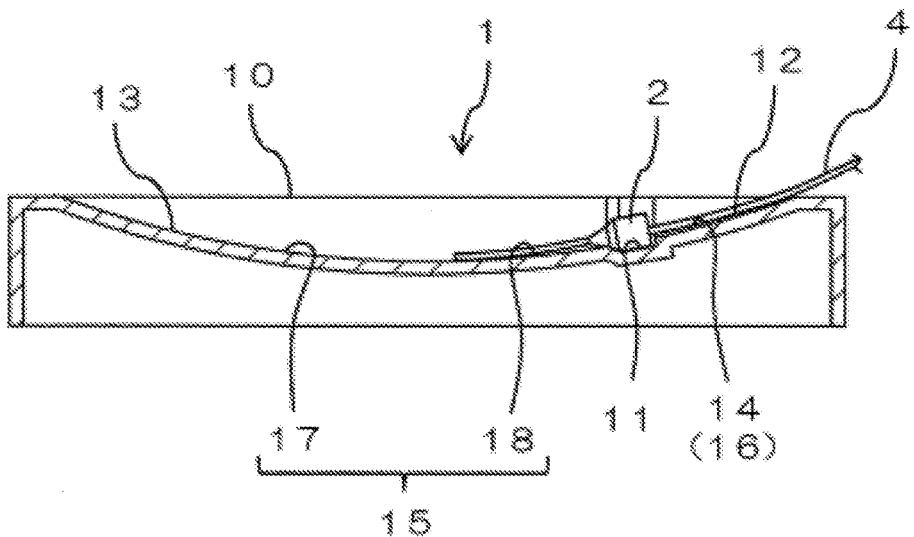
FIG. 6B is a schematic cross-sectional view for explaining an embodiment at the time of inserting a column into the ferrule.

Thereafter, by further inserting the column 4 into the ferrule 2, the tip end part of the column 4 inserted into the ferrule 2 is guided along the third inclined surface 18 (see FIG. 6B). With this, the tip end part of the column 4 is once guided obliquely downward. Thereafter, when the column 4 is further inserted into the ferrule 2, the tip end part of the column 4 is guided along the second inclined surface 17 (see FIG. 6C).

Figure 6C:
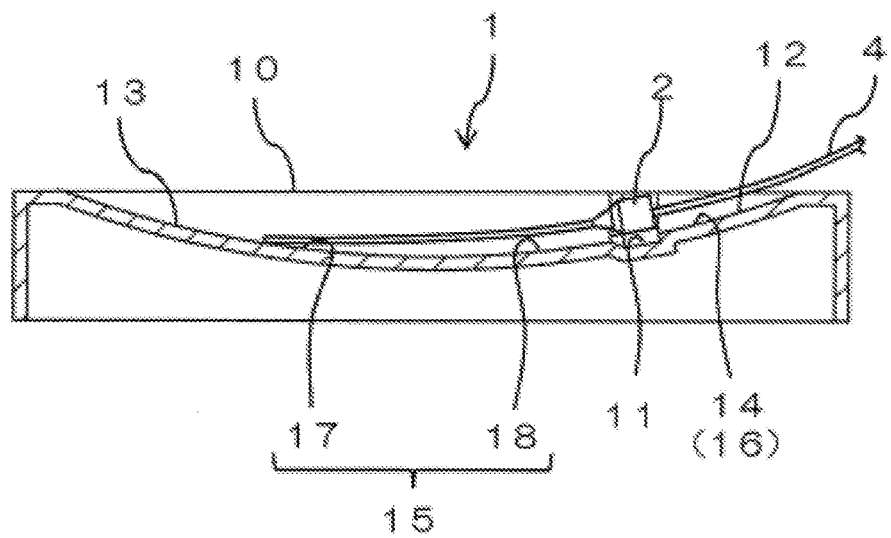
FIG. 6C is a schematic cross-sectional view for explaining an embodiment at the time of inserting a column into the ferrule.
Figure 6D:
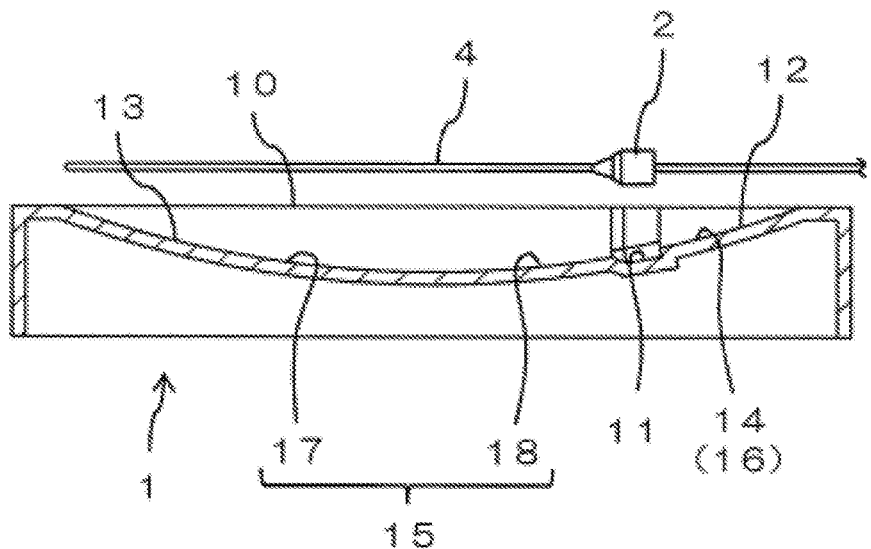
FIG. 6D is a schematic cross-sectional view for explaining an embodiment at the time of inserting a column into the ferrule.
Figure 7:
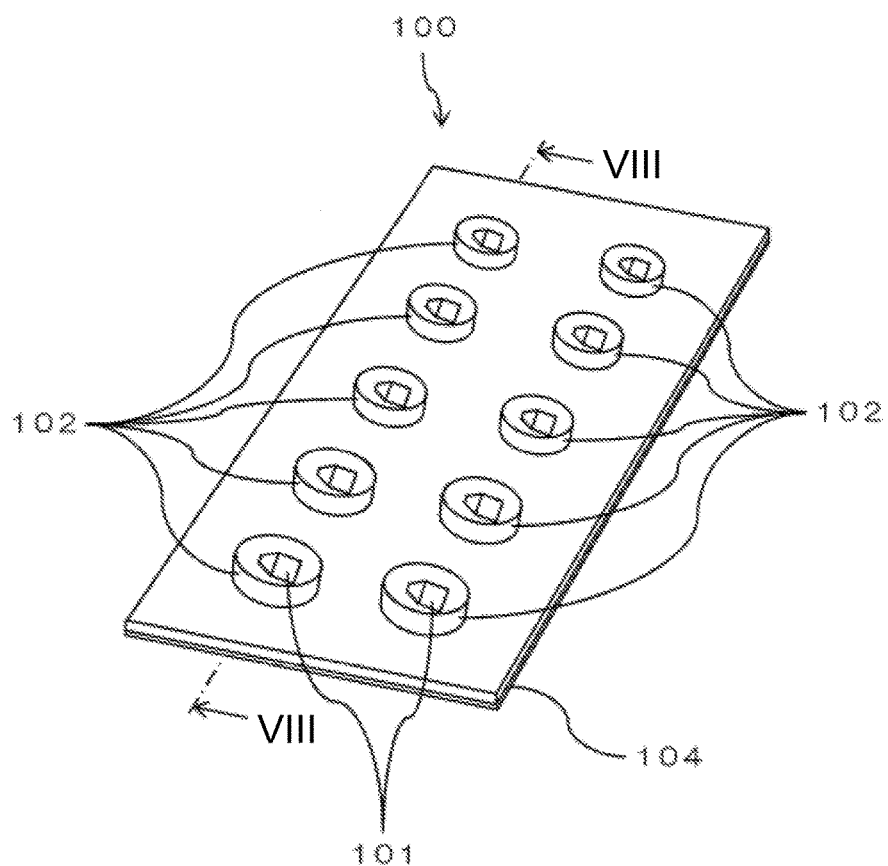
FIG. 7 is a perspective view showing a configuration example of a conventional ferrule container.
Figure 8:
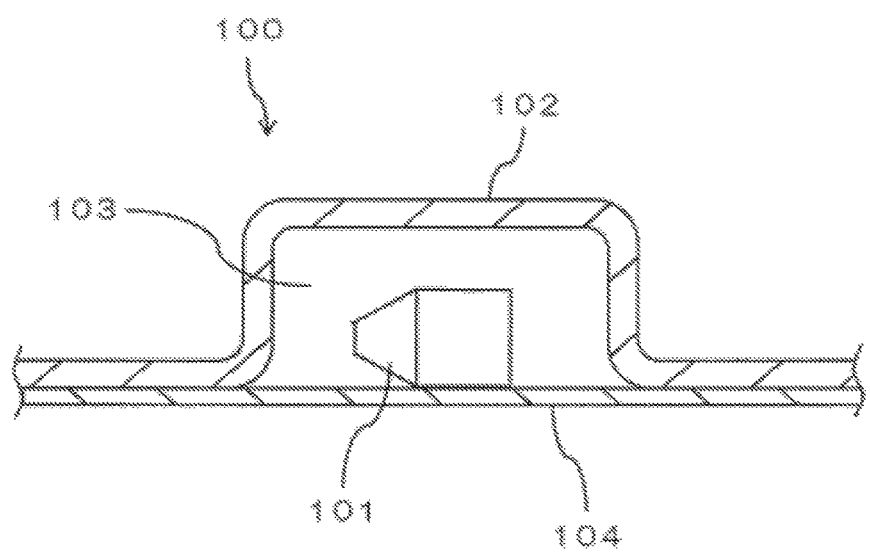
FIG. 8 is a cross-sectional view partially showing a VIII-VIII cross-section of the ferrule container shown in FIG. 7.

The tip end part of the column 4 after inserted into the ferrule 2 becomes a curved state during the tip end part is guided along the second inclined surface 17. When the column 4 is further inserted into the ferrule 2, as shown in FIG. 6C, the ferrule 2 can be lifted up from the ferrule accommodating part 11 by the restoring force of the column 4. With this, after inserting the column 4 into the ferrule 2, the ferrule 2 can be smoothly taken out from the ferrule container 1 together with the column 4 (see FIG. 6D). Therefore, the work for inserting the column 4 into the ferrule 2 can be more easily performed.

As explained above, in the case of using a ferrule container containing ferrules in which ferrules 2 are accommodated in ferrule accommodating parts 11, it is possible to insert a column 4 into the ferrule 2 while keeping a state in which the ferrule 2 is accommodated in the ferrule accommodating part 11. With this, before inserting the column 4 into the ferrule 2, it is not at all necessary for an operator to bring the hand into contact with the ferrule 2. Consequently, unlike a case in which an operator inserts a column 4 while pinching a ferrule 2 with hand, the insertion work of a column 4 into a ferrule 2 can be more easily performed, and foreign objects are less likely to adhere to the ferrule 2.

It is also possible not only to provide a ferrule container containing a ferrule, but also to provide a ferrule container 1 in a state in which no ferrule 2 is accommodated in the ferrule accommodating part 11. In this case, since the ferrule container 1 is used such that the ferrule 2 is accommodated in the ferrule accommodating part 11, the ferrule container 1 functions as a jig for inserting the column 4 into the ferrule 2.

In the aforementioned embodiment, the description is directed to a configuration in which the column 4 is guided by the first inclined surface 16, the second inclined surface 17, and the third inclined surface 18. However, the configuration is not limited to the above, and it may be configured such that at least one of the first inclined surface 16, the second inclined surface 17, and the third inclined surface 18 is omitted.

For example, it may be configured such that all of the first inclined surface 16, the second inclined surface 17, and the third inclined surface 18 are omitted, and that the first column guide part 12 and the second column guide part 13 guide the column 4 along the horizontal direction. In this case, the ferrule accommodating part 11 is not limited to the configuration in which the ferrule 2 is accommodated in an inclined posture, and may be configured such that, for example, the ferrule 2 is accommodated in a posture of extending in the horizontal direction.

Further, it may be configured such that the second column guide part 13 is omitted and only the first column guide part 12 is provided at the ferrule container 1. Even with this configuration, guiding of the column 4 by the first column guide part 12 enables a smooth and reliable insertion of the column 4 into the ferrule 2 accommodated in the ferrule accommodating part 11.

DESCRIPTION OF SYMBOLS 1 ferrule container
2 ferrule
3 cover film
4 column
10 top wall
11 ferrule accommodating part
12 first column guide part
13 second column guide part
14 curved surface
15 curved surface
16 first inclined surface
17 second inclined surface
18 third inclined surface
20 side wall
21 insertion hole
22 first conical surface
23 second conical surface
24 cylindrical surface
25 swaging part
26 end face
27 dent
31 grip portion
D1 insertion direction
D2 width direction

The invention claimed is:

1. A ferrule container containing a ferrule, comprising:
a ferrule accommodating part configured to accommodate the ferrule; and
a first column guide part configured to guide a column so as to insert the column into the ferrule accommodated in the ferrule accommodating part; and
a ferrule accommodated in the ferrule accommodating part.

2. The ferrule container containing a ferrule according to claim 1,
wherein the ferrule container is provided with a plurality of ferrule accommodating parts, and
wherein the ferrule container is further provided with a plurality of cover films that individually cover each ferrule accommodating part and are capable of being peeled from the ferrule container.

3. The ferrule container containing a ferrule according to claim 1,
wherein a conically-shaped dent is formed at an end face of the ferrule on a first column guide part side so as to expand larger than an outer diameter of a column to be inserted so that the column is inserted into the ferrule via the dent.

4. The ferrule container according to claim 1, further comprising:
a top wall configured to surround the ferrule accommodating part and the first column guide part, and
wherein the ferrule accommodating part is configured to accommodate the ferrule at an angle inclined obliquely relative to a planar upper surface of the top wall.

5. The ferrule container according to claim 4, wherein the top wall, the first column guide part, and the ferrule accommodating part are integrally formed.

6. The ferrule container according to claim 1, wherein the first column guide part includes a first inclined surface that gradually becomes lower toward the ferrule accommodating part.

7. The ferrule container according to claim 1, further comprising:
a second column guide part configured to guide a tip end part of the column after being inserted into the ferrule.

* * * * *